United States Patent [19]

Boswell, Jr. et al.

[11] 4,020,112
[45] Apr. 26, 1977

[54] OXIDATIVE FLUORINATION OF PHENOLS

[75] Inventors: George Albert Boswell, Jr., Wilmington, Del.; Charles William Tullock, Landenberg, Pa.

[73] Assignee: E. I. Du Pont de Nemours and Company, Wilmington, Del.

[22] Filed: Feb. 6, 1975

[21] Appl. No.: 547,495

[52] U.S. Cl. .................. 260/612 R; 260/543 H; 260/505 R; 260/513 R; 260/586 R; 260/590 PA; 260/650 F; 260/648 R; 260/609 R; 260/470

[51] Int. Cl.² .......................................... C07C 43/20

[58] Field of Search ............... 260/590 R, 612 R

[56] References Cited

UNITED STATES PATENTS 2,859,245  11/1958  Smith ........................... 260/615 F

OTHER PUBLICATIONS

Hasek et al., J.A.C.S., vol. 82, pp. 543–551, (1960).
Reaktssii i metody issledsvannica organicheskukh, M.M. III emrkuha, pp. 40–63, (1971).

*Primary Examiner*—James O. Thomas, Jr.
*Assistant Examiner*—James H. Reamer

[57] ABSTRACT

Phenols are oxidatively fluorinated by reaction with sulfur tetrafluoride in hydrogen fluoride solution at about 0° to 250° C. to form products which are useful as solvents and/or plasticizers for polymers. The novel products of this process include 1-fluoro-2-hydro-2,5-cyclohexadienes of the structure

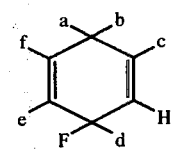

where
  *a* and *b* are fluorine, or together are carbonyl oxygen,
  *c* and *f*, alike or different, are chlorine, bromine, CF₃ or SO₂F,
  *e* is hydrogen, chlorine or SO₂F, and
  *d* is chlorine or fluorine, or
  *e* and *f* together are 1,3-butadien-1,4-diyl;
and 1,1,3,5-tetrafluoro-2,4,6-trihalo-4-(3,5-difluoro-2,4,6-trihalophenoxy)-2,5-cyclohexadienes of the structure

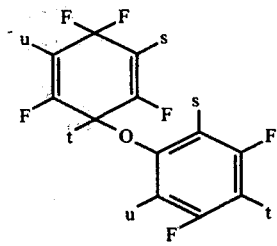

where s, t and u, alike or different, are chlorine, bromine or fluorine.

2 Claims, No Drawings

OXIDATIVE FLUORINATION OF PHENOLS

BACKGROUND OF THE INVENTION

1. Field of the Invention

This invention relates to the oxidative fluorination of various phenols by reaction with sulfur tetrafluoride in hydrogen fluoride solution. It also relates to certain novel fluorohydrocyclohexadienes, fluorohydrocyclohexadienones and perhalo-4-(perhalophenoxy)-2,5-cyclohexadienes that are useful as solvents and/or plasticizers for polymers.

2. Description of the Prior Art

No published reports of any reactions involving a phenol and sulfur tetrafluoride ($SF_4$) are known. However, a number of examples of reaction between organic alcohols and $SF_4$ are known, often with the result of replacing the hydroxyl with fluorine. Hydrogen fluoride (HF) is a well recognized catalyst for the replacement of carbonyl oxygen with two fluorines by means of $SF_4$ (Smith, U.S. Pat. No. 2,859,245). Aliphatic, cycloaliphatic and aromatic compounds containing Cl and/or Br are disclosed to react with $SF_4$ to replace Cl and Br with F using HF as a catalyst (Smith, U.S. Pat. No. 2,937,171). Carboxylic acids containing primary and secondary amino groups are successfully converted to corresponding trifluoromethyl amines in HF medium (Raasch, Jour. Org. Chem., vol. 27, p. 1406–1409, 1962).

Tetrachloro-p-quinone is reported to react with $SF_4$ in the presence of HF to form 1,1,4,4-tetrafluorotetrachloro-2,5-cyclohexadiene and 4,4-difluoro-2,3,5,6-tetrachloro-2,5-cyclohexadien-1-one (Hasek et al., Jour. Am. Chem. Soc., Vol. 82, p. 543, 1960).

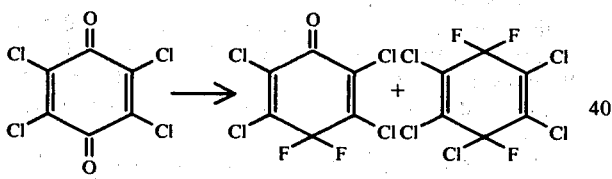

Likewise, tetrafluoro-p-quinone and 2,6-dichloro 3,5-difluoro-1,4-quinone are reported to give octafluoro-1,4-cyclohexadiene and 1,5-dichlorohexafluoro-1,4-cyclohexadiene, respectively (Shteingarts and Oksenenko, Jour. Org. Chem. (U.S.S.R.), Vol. 6, p. 1623, 1970).

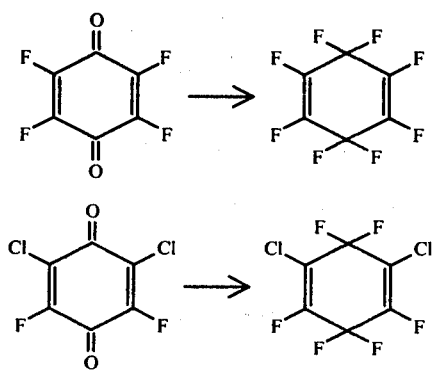

Similarly, 9-keto-9,10-dihydroanthracene is reacted with $SF_4$ in the presence of HF as catalyst to give 10,10-difluoro-9-keto-9,10-dihydroanthracene (Applequist and Searle, Jour. Org. Chem., vol. 29, p. 987, 1964).

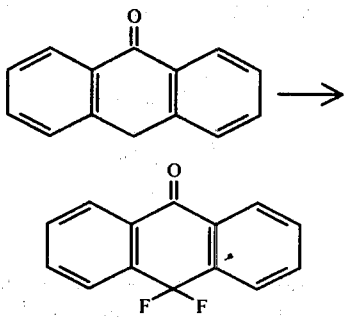

Shteingarts et al. (Jour. Org. Chem., U.S.S.R., Vol. 37, p. 1537, 1967) show that pentafluoro-4-nitrocyclohexa-2,5-dien-1-one, formed by the action of nitrating agents on an excess of pentafluorophenol, on decomposing in an excess of the initial phenol, forms pentafluoro-4-(pentafluorophenoxy)cyclohexa-2,5-dien-1-one.

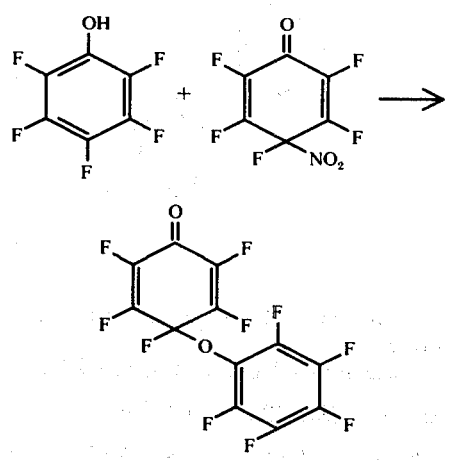

SUMMARY OF THE INVENTION

This invention is based on the discovery that when a phenol is reacted with sulfur tetrafluoride in hydrogen fluoride solution oxidative fluorination takes place. The method of this invention comprises reacting a phenol of the structure

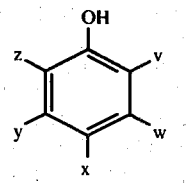

where
  v, w, y and z, alike or different, are hydrogen, chlorine, bromine, fluorine, $CH_3$, $C_6H_5$, $CO_2CH_3$, COOH, $OCH_3$ or $SO_3M$ where M is alkali metal, and
  x is hydrogen, chlorine, bromine, fluorine, $CH_3$, $C_6H_5$, $CO_2CH_3$, COOH, $OCH_3$, $SO_3M$ or OH, or
  x and y together, or y and z together, are 1,3-butadien-1,4-diyl, with sulfur tetrafluoride in hydrogen fluoride solution at a temperature of about 0° to 250° C.

This reaction produces novel 1-fluoro-2-hydro-2,5-cyclohexadienes of the structure

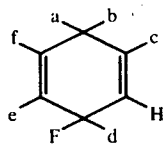

where
- a and b are fluorine, or together are carbonyl oxygen,
- c and f, alike or different, are chlorine, bromine, CF₃ or SO₂F,
- e is hydrogen, chlorine or SO₂F, and
- d is chlorine or fluorine, or
- e and f together are 1,3-butadien-1,4-diyl, and novel 1,1,3,5-tetrafluoro-2,4,6-trihalo-4-(3,5-difluoro-2,4,6-trihalophenoxy)-2,5-cyclohexadienes of the structure

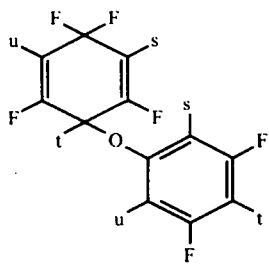

where
- s, t and u, alike or different, are chlorine, bromine or fluorine, which are useful as solvents and/or plasticizers.

DETAILED DESCRIPTION OF THE INVENTION

Not only have phenols not been reacted with sulfur tetrafluoride in hydrogen fluoride solution heretofore, but this reaction takes the course of a controlled oxidative fluorination rather than a normal fluorination as is generally obtained when organic compounds are reacted with sulfur tetrafluoride.

In operating the process of this invention a suitable pressure reactor is charged with a mixture containing a phenol, HF, SF₄ and, optionally, an inert solvent such as dichloromethane. The amount of SF₄ present may vary from about 0.1 to 10 moles per mole of phenol and preferably from about 0.5 to 5.0 moles. The amount of HF should be sufficient to keep the reactants in solution. The reaction is brought about by closing the reactor and agitating with the contents under a pressure of about 15 to 1500 psi and a temperature in the range of about 0°–250° C. for a period of about 1 to 24 hours. Preferably the reaction is carried out under autogeneous pressure at a temperature of about 25° to 100° C. for about 2 to 16 hours.

After the reaction has proceeded for the desired period of time, the reactor is opened, volatile materials are vented, and residual HF is removed by heating or by reaction with added pellets of sodium fluoride. The products are isolated by conventional techniques which may include, but are not limited to, distillation, steam distillation, crystallization, extraction, partition chromatography or combinations of these procedures. Sulfur halides can be removed by means of aqueous alkali.

The novel 1-fluoro-2-hydro-2,5-cyclohexadienes of the structure

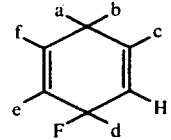

where
- a and b are fluorine, or together are carbonyl oxygen,
- c and f, alike or different, are chlorine, bromine, CF₃ or SO₂F,
- e is hydrogen, chlorine or SO₂F, and
- d is chlorine or fluorine, or
- e and f, together are 1,3-butadien-1,4-diyl, are prepared by reacting a phenol of the structure

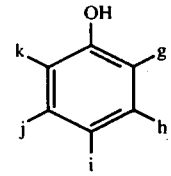

where
- g and k, alike or different, are chlorine, bromine or COOH,
- h and j, alike or different, are hydrogen, chlorine or SO₃M where M is alkali metal, and
- i is hydrogen, chlorine, bromine, or hydroxyl, or
- j and k together are 1,3-butadien-1,4-diyl, with sulfur tetrafluoride in hydrogen fluoride solution at a temperature of about 0° to 250° C. The preferred fluorocyclohexadienes are 1,1,4,4-tetrafluoro-2,5-cyclohexadienes and 1,1-difluoro-2,5-cyclohexadien-4-ones.

The novel 1,1,3,5-tetrafluoro-2,4,6-trihalo-4-(3,5-difluoro-2,4,6-trihalophenoxy)-2,5-cyclohexadienes of the structure

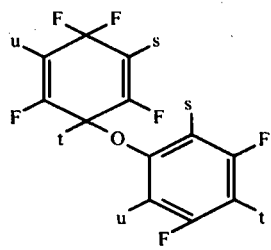

where s, t and u, alike or different, are chlorine, bromine or fluorine are prepared by reacting a 3,5-difluoro-2,4,6-trihalophenol of the structure

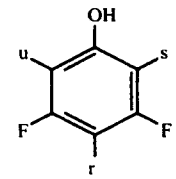

wherein r is hydrogen, chlorine, bromine or fluorine, with sulfur tetrafluoride in hydrogen fluoride solution at a temperature of about 0° to 250° C. In this reaction s is the same as r or fluorine, except that, when r is hydrogen, s is fluorine.

The novel 1-fluoro-2,5-cyclohexadienes are solvents for polystyrene, poly(methyl methacrylate) and poly(vinyl acetate). The novel 1,1,3,5-tetrafluoro-2,4,6-trihalo-4-(3,5-difluoro-2,4,6-trihalophenoxy)-2,5-cyclohexadienes are plasticizers for polystyrene, poly(methyl methacrylate and poly(vinyl acetate). Some of the 1-fluoro-2,5-cyclohexadienes are sufficiently nonvolatile to function also as plasticizers for these polymers. In addition, all of these hexadienes can be polymerized by means of di(t-butyl) peroxide initiator to low molecular weight homopolymers which can function as plasticizers for the above polymers. These polymeric hexadienes can also be used as water repellants for cellulosic materials.

EXAMPLES OF THE INVENTION

The following examples, illustrating the novel process of this invention and the preparation and use of the novel products of this invention, are given without any intention that the invention be limited thereto. In these examples temperatures are given in degrees centrigrade and all percentages are by weight. Analyses include determinations by elemental analysis (EA), infrared spectroscopy (IR), mass spectroscopy (MS), nuclear magnetic resonance (NMR), vapor phase chromatography (VPC), and electron spectroscopy for chemical analysis (ESCA).

EXAMPLE 1

Reaction of Pentachlorophenol with $SF_4$ in HF

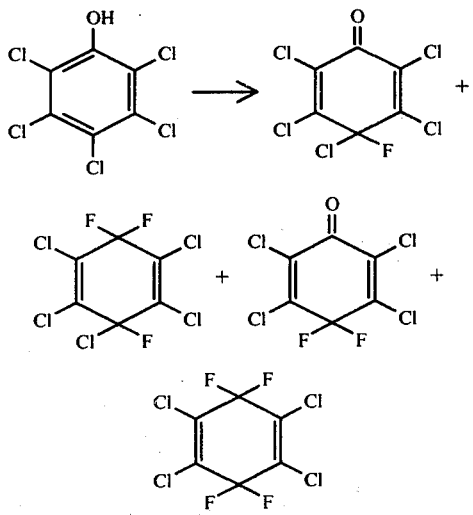

Air-free mixtures of pentachlorophenol ($C_6Cl_5OH$), $SF_4$ and HF were heated with agitation under autogenous pressure in Hastelloy pressure reactors. The reaction mixtures were cooled to room temperature, volatile materials were vented, and the residues were heated moderately to remove much of the remaining hydrogen fluoride. The crude products were then subjected to steam distillation, the distillates were extracted with dichloromethane, and the extracts were distilled. Data for the runs are given in Table I.

TABLE I

| Run | $C_6Cl_5OH$ (g) | $SF_4$ (g) | HF (g) | $SF_4/C_6Cl_5OH$ Mole Ratio | Temp. (° C) | Time (hrs.) |
|---|---|---|---|---|---|---|
| A | 102 | 97 | 45 | 2.36/1 | 100 | 6 |
| B | 43 | 24 | 40 | 1.37/1 | 50 | 1 |
|   |    |    |    |        | 75 | 1 } successively |
|   |    |    |    |        | 100 | 1 |
| C | 70 | 45 | 40 | 1.59/1 | 100 | 3 |
| D | 70 | 29 | 40 | 1.02/1 | 100 | 3 |

In run A two principal product fractions are obtained: (1) 60.3 g, bp 91°–97°–97°/31 mm, mp 30°; (2) 18.6 g, semisolid residue. Fraction (1) was identified as 1,1,4,4-tetrafluorotetrachloro-2,5-cyclohexadiene by comparison of its IR and MS data with those of a known sample of the compound (Hasek et al., Jour. Am. Chem. Soc., vol. 82, p. 543, 1960) Fraction (2) was indicated by fluorine NMR, IR, VPC and EA analyses to be a mixture of isomeric 1,1,4-trifluoropentachloro-2,5-cyclohexadiene and 1,5,6-trifluoropentachloro-1,3-cyclohexadiene.

EA. Calcd for $C_6Cl_5F_3$: C, 23.49; Cl, 57.91; F, 18.60; Found: C, 23.80; Cl, 57.87; F, 18.50.

In run B an additional product fraction, bp 102°–3°/1.8 mm, was identified as containing about 81% of 4-fluoropentachloro-2,5-cyclohexadien-1-one by VPC, IR and fluorine NMR analyses.

In run C the principal products were 37.65 g of 1,1,4,4-tetrafluorotetrachloro-2,5-cyclohexadiene, 4.61 g of a $C_6Cl_5F_3$ isomer mixture of 1,1,4-trifluoropentachloro-2,5-cyclohexadiene and 1,5,6-trifluoropentachloro-1,3-cyclohexadiene, and 9.66 g of 4-fluoropentachloro-2,5-cyclohexadien-1-one. The ketone fraction, bp ~116°/10 mm, was indicated by MS analysis to contain about 7% of 4,4-difluorotetrachloro-2,5-cyclohexadien-1-one.

EA. Calcd for $C_6Cl_5FO$: C, 25.31; Cl, 62.39; F, 6.68; Found: C, 26.07; Cl, 61.89; F, 6.93.

In run D the principal products were 22.04 g of 1,1,4-trifluoropentachloro-2,5-cyclohexadiene (bp 45°–48°/0.26 to 0.7 mm) and 16.73 g of solid 4-fluoropentachloro-2,5-cyclohexadien-1-one (bp 82°–85°/0.10 to 0.15 mm; mp 59°–65°).

EXAMPLE 2

Reaction of 2,3,4,6-Tetrachlorophenol with $SF_4$ in HF

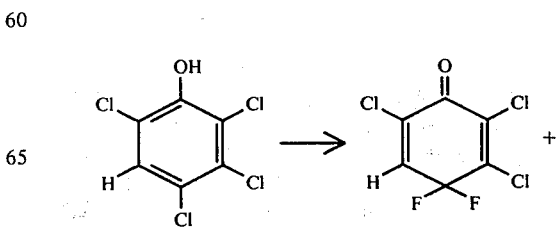

-continued

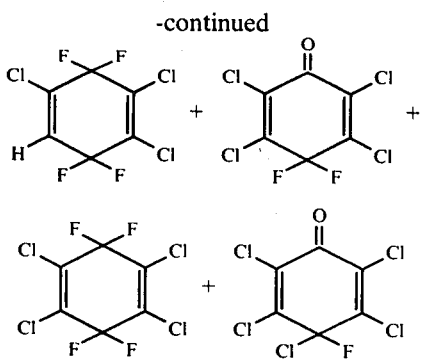

Following the procedure of Example 1, 2,3,4,6-tetrachlorophenol ($C_6HCl_4OH$) was reacted with $SF_4$ in HF medium. The data for two runs are given in Table II.

TABLE II

| Run | $C_6HCl_4OH$ (g) | $SF_4$ (g) | HF (g) | $SF_4/C_6HCl_4OH$ Mole Ratio | Temp. (°C) | Time (Hrs) |
|---|---|---|---|---|---|---|
| A | 93.0 | 97 | 45 | 2.25/1 | Ambient air | 16 |
| B | 46.4 | 25 | 40 | 1.15/1 | 25<br>50 | 4 successively<br>2 |

In run A the crude steam-distilled product amounted to 60 g and the non-steam-distillable residue amounted to 15 g. The residue was a soft brown resin which contained a small amount of elemental sulfur and was largely soluble in acetone, ethyl acetate, diethyl ether, petroleum ether, benzene, dichloromethane or carbon disulfide but was otherwise not characterized. The steam-distilled product was fractionally distilled to yield three principal fractions: (1) 43.99 g, bp 69.0°–70.6°/22 mm; (2) 3.82 g, bp 88°–97°/22 mm; (3) 1.03 g, bp 88°–90°/0.2–0.5 mm, yellow solid. Fraction (1) was identified as 1,1,4,4-tetrafluoro-2,3,6-trichloro-2,5-cyclohexadiene by fluorine NMR and EA.

EA. Calcd for $C_6HCl_3F_4$: C, 28.18; H, 0.39; Cl, 41.68; F, 29.75; Found: C, 28.36; H, 0.47; Cl, 44.09; F, 29.97.

Fraction (2) was identified by fluorine NMR as 1,1,4,4-tetrafluorotetrachloro-2,5-cyclohexadiene. Fraction (3) was indicated by VPC to contain two components which were identified by MS analysis as 4,4-difluorotetrachloro-2,5-cyclohexadien-1-one and 4-fluoropentachloro-2,5-cyclohexadien-1-one.

In run B the steam-distilled product weighed 32.5 g and the brown, viscous, syrupy residue weighed 11 g. The steam distillate contained 5.67 g of 1,1,4,4-tetrafluoro-2,3,6-trichloro-2,5-cyclohexadiene, 4.68 g of yellow, liquid 4,4-difluoro-2,3,6-trichloro-2,5-cyclohexadien-1-one (bp 52°–61°/0.7 mm), and 1.4 g of yellow, solid, nearly pure 4-fluoropentachloro-2,5-cyclohexadien-1-one.

Polystyrene, poly(methyl methacrylate) and poly(vinyl acetate) were each found to yield stable solutions at room temperature in 1,1,4,4-tetrafluoro-2,3,6-trichloro-2,5-cyclohexadiene. When mixed with di(t-butyl) peroxide initiator and heated gradually to 211° over a period of about 3 hours, about a third of the cyclohexadiene was converted to a soft nonflowable polymer which was an effective plasticizer for the above host polymers when used at the level of 9–10%. Cellulose filter paper was dipped into a solution of the polymeric cyclohexadiene and dried, and the treated paper became water-repellant.

4,4-Difluoro-2,3,6-trichloro-2,5-cyclohexadien-1-one was found to be an effective plasticizer for polystyrene and poly(methyl methacrylate) when incorporated into the polymers at the level of 9%.

EXAMPLE 3

Reaction of 2,4,6-Trichlorophenol with $SF_4$ in HF

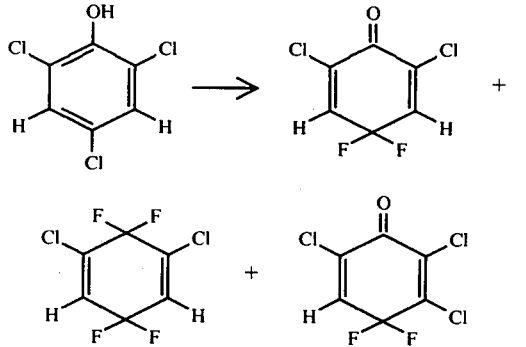

2,4,6-Trichlorophenol ($C_6H_2Cl_3OH$) was reacted with $SF_4$ in HF, the data for three runs being given in Table III.

TABLE III

| Run | $C_6H_2Cl_3OH$ (g) | $SF_4$ (g) | HF (g) | $SF_4/C_6H_2Cl_3OH$ Mole Ratio | Temp. (°C) | Time (Hrs) |
|---|---|---|---|---|---|---|
| A | 39.5 | 86 | 20 | 4.00/1 | 35<br>50<br>65 | 1<br>1 successively<br>4 |
| B | 79.0 | 97 | 45 | 2.25/1 | Ambient air | 16 |
| C | 79.0 | 25 | 50 | 0.57/1 | Ambient air | 16 |

In run A the reaction mixture was diluted with 50 ml of dichloromethane and after removing most of the HF by gentle heat the composite was stored over sodium fluoride pellets to remove remaining HF. The dichloromethane solution was then fractionally distilled to give 25 g of yellow liquid, bp 25°–27°/0.15 mm. The distillate contained sulfur dichloride ($S_2Cl_2$), which was removed by washing with 10% aqueous sodium hydroxide. The washed material was fractionated to yield 6.46 g of product, bp 54.4°–57.0°/45 mm, indicated by VPC to be substantially pure, by MS and EA to have a molecular formula of $C_6H_2Cl_2F_4$, and by IR and NMR to be 1,1,4,4-tetrafluoro-2,6-dichloro-2,5-cyclohexadiene.

EA. Calcd for $C_6H_2Cl_2F_4$: C, 32.58; H, 0.90; Cl, 32.13; F, 34.39; Found: C, 32.62; H, 1.12; Cl, 31.71; F, 34.18.

In run B the steam distillation procedure was used, and 57.3 g of crude steam distillate was obtained. Extraction of the non-steam distillable residue (17 g) with acetone left 4.0 g of insoluble elemental sulfur. The acetone soluble fraction was distilled to yield 2.94 g of a yellow-brown viscous distillate, bp 102°–138°/0.08–0.20 mm; which was not characterized. The steam-distilled product was fractionally distilled to yield 44.5 g, bp 58°/40 mm, of pure 1,1,4,4-tetrafluoro-2,6-dichloro-2,5-cyclohexadiene.

In run C the steam distillate yielded little, if any, 1,1,4,4-tetrafluoro-2,6-dichloro-2,5-cyclohexadiene and two other products identified as 4,4-difluoro-2,6-dichloro-2,5-cyclohexadien-1-one, bp 31.4°–46.4°/0.12–1.5 mm and 4,4-difluoro-2,3,6-trichloro-2,5-cyclohexadien-1-one, bp 36°–45°/0.10–0.27 mm (cf. Example 2).

Polystyrene, poly(methyl methacrylate) and poly(vinyl acetate) were each found to be soluble in 1,1,4,4-tetrafluoro-2,6-dichloro-2,5-cyclohexadiene, the solutions being stable at 25°. The diene also polymerized to the extent of about 15% when heated from 122° to 156° over a period of about 7 hours with di(t-butyl) peroxide initiator, the polymer being a clear soft nonflowable material soluble in dichloromethane.

4,4-Difluoro-2,6-dichloro-2,5-cyclohexadien-1-one was incorporated into each of polystyrene and poly(methyl methacrylate) at the level of 9%, and the resultant polymers were effectively plasticized.

EXAMPLE 4

Reaction of 2,6-Dichlorophenol with $SF_4$ in HF

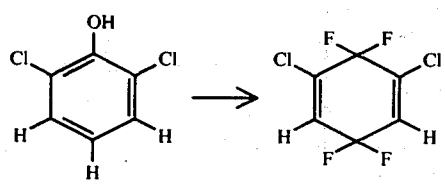

An air-free mixture of 32.6 g of 2,6-dichlorophenol, 86 g of $SF_4$ ($SF_4$/dichlorophenol mole ratio = 4/1) and 40 g of HF was agitated for 16 hours at room temperature in a sealed Hastelloy reactor. The crude vented product yielded 7.2 g of yellow steam distillate and 19 g of yellow-orange solid steam distillation residue. The steam distillate was fractionated to give 6.78 g of 1,1,4,4-tetrafluoro-2,6-dichloro-2,5-cyclohexadiene, bp 52°/30 mm. The non-steam distillable product was extracted with 10% aqueous potassium hydroxide and the alkali-soluble fraction recovered by acidification with 12% hydrochloric acid. The recovered alkali-soluble material was exhaustively extracted with boiling tetrahydrofuran (THF) and the resulting THF-insoluble, cream colored solid, mp 265°, was found by EA and MW analyses to correspond to material having 18 carbon atoms.

Calcd for $C_{18}H_8Cl_6SO_2$: C, 43.11; H, 1.60; Cl, 42.51; S, 6.39; F, 0.00; MW, 501; Found: C, 41.22; H, 2.15; Cl, 38.48; S, 6.12; F, 0.74; MW, 483.

EXAMPLE 5

Reaction of 2,4,6-Tribromophenol with $SF_4$ in HF

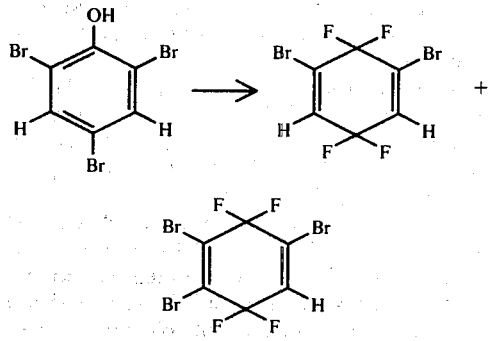

An air-free mixture of 33.1 g of 2,4,6-tribromophenol, 45 g of $SF_4$ ($SF_4$/tribromophenol mole ratio = 4.2/1) and 30 g of HF was agitated at room temperature for 16 hours in a sealed Hastelloy reactor. The vented crude product was steam-distilled to yield 7.5 g of liquid nonaqueous distillate and 27.6 g of tan solid residue. The liquid distillate was analyzed by VPC, MS, fluorine NMR and differential thermal analyses (DTA), and was found to contain approximately equal amounts of 1,1,4,4-tetrafluoro-2,6-dibromo-2,5-cyclohexadiene (mp 21°, bp 177°) and 1,1,4,4-tetrafluoro-2,5,6-tribromo-2,5-cyclohexadiene (mp 11°, bp 227°). A polymeric component of the residue, isolated as insoluble material via acetone extraction, was indicated by EA probably to contain 24 carbons in the form of four interconnected brominated phenyl groups.

Polystyrene, poly(methyl methacrylate) and poly(vinyl acetate) were each found to be effectively plasticized by incorporation into them of 9–10% of 1,1,4,4-tetrafluoro-2,6-dibromo-2,5-cyclohexadiene or1,1,4,4-tetrafluoro-2,5,6-tribromo-2,5-cyclohexadiene.

1,1,4,4-Tetrafluoro-2,6-dibromo-2,5-cyclohexadiene was polymerized to the extent of about 32% when heated from 128° to 154° over a period of about 4 hours with di(t-butyl) peroxide initiator, the polymer being a soft solid product which was soluble in acetone.

EXAMPLE 6

Reaction of 1-Hydroxy-2-naphthoic Acid with $SF_4$ in HF

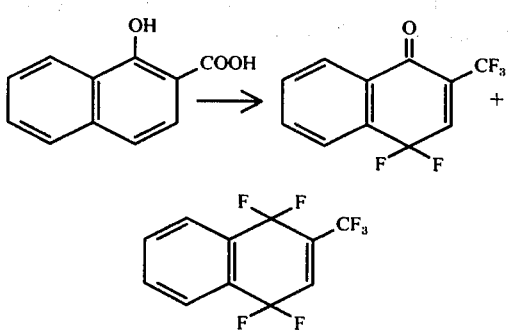

An air-free mixture of 28.2 g of 1-hydroxy-2-naphthoic acid, 108 g of $SF_4$ ($SF_4$/hydroxynaphthoic acid mole ratio = 6.7/1) and 50 g of HF was agitated at 25° for 2 hours, 65° for 2 hours, 100° for 2 hours and room temperature for 12 hours. The vented reaction mixture was extracted with methylene chloride and the extract distilled at stillpot temperatures up to 190°/0.2 mm. Chromatographically separated fractions of the distillate were identified by IR and NMR as 4,4-difluoro-1-keto-2-trifluoromethyl-1,4-dihydronaphthalene (A) and 1,1,4,4-tetrafluoro-2-trifluoromethyl-1,4-dihydronaphthalene (B).

A. Anal Calcd for $C_{11}H_5F_5O$: C, 53.23; H, 2.02; F, 38.31; Found: C, 52.55; H, 1.97; F, 38.29; mp, 53°-60°

B. Anal. Calcd for $C_{11}H_5F_7$: C, 48.89; H, 1.85; F, 49.26; Found: C, 48.78; H, 1.99; F, 49.77. mp (DTA), 8-9.5°; bp (DTA), 187.5°-188°.

In a separate run the above mixture of reactants was agitated at 10° for 2 hours, 20° for 2 hours and room temperature for 12 hours. The vented reaction mixture yielded 4.5 g of product A, bp 73°/0.38-0.55 mm, mp 50°-55°, and 12 g of nondistillable red solid residue which did not melt below 350°.

EXAMPLE 7

Reaction of Sodium 2,5-Dihydroxybenzenesulfonate with $SF_4$ in HF

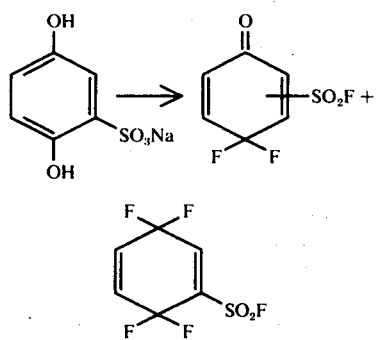

An air-free mixture of 21.2 g of sodium 2,5-dihydroxybenzenesulfonate [$C_6H_3(OH)_2SO_3Na$], 43 g of $SF_4$ [$SF_4/C_6H_3(OH)_2SO_3Na$ mole ratio = 4/1] and 40 g of HF was agitated at 25° for 4 hours, 35° for 1 hour and 50° for 3 hours. The vented crude product was extracted with 100 ml of dichloromethane, and the extract was concentrated on a steam bath to yield 12.1 g of semisolid product which was further separated by filtration into liquid and solid portions.

The liquid portion was fractionally distilled to yield fractions boiling at 31°-33°/0.5 mm and 49°-55°/0.5 mm, respectively. The lower-boiling fraction was identified by IR, NMR and EA as 3,3,6,6-tetrafluoro-1,4-cyclohexadienylsulfonyl fluoride.

Calcd for $C_6H_3F_5O_2S$: C, 30.77; H, 1.28; F, 40.60; Found: C, 31.35; H, 1.45, F, 39.66.

The higher-boiling fraction was similarly identified as a 1,1-difluoro-4-keto-2,5-cyclohexadienylsulfonyl fluoride, the position of the sulfonyl fluoride group being indeterminate.

Calcd for $C_6H_3F_3O_3S$: C, 33.96; H, 1.42; F, 26.89; Found: C, 33.79; H, 1.61; F, 27.75.

The solid portion was recrystallized from benzene to yield a yellow-brown product, mp 93°-5°, which was identified by IR and EA as 2,5-dihydroxybenzenesulfonyl fluoride.

Calcd for $C_6H_5FO_4S$: C, 37.50; H, 2.60; S, 16.66; Found: C, 36.85; H, 2.64; S, 16.75.

EXAMPLE 8

Reaction of Pentafluorophenol with $SF_4$ in HF

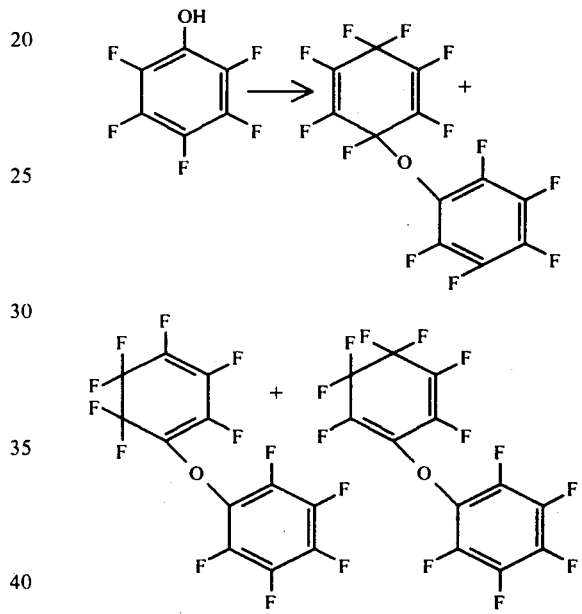

Air-free mixtures of pentafluorophenol ($C_6F_5OH$), $SF_4$ and HF were heated with agitation under autogenous pressure in Hastelloy pressure reactors. The reaction mixtures were cooled to room temperature, volatile materials were vented, and the residues heated moderately to remove much of the remaining hydrogen fluoride. The crude products were then steam distillated, the sought products extracted from the distillate into dichloromethane, and the resultant solution fractionally distilled. Data for three runs are given in Table IV.

TABLE IV

| Run | $C_6F_5OH$ (g) | $SF_4$ (g) | HF (g) | $SF_4/C_6F_5OH$ Mole Ratio | Temp. (° C) | Time (Hrs) |
|---|---|---|---|---|---|---|
| A | 25.0 | 45 | 25 | 3.06/1 | Ambient air | 16* |
| B | 25.0 | 45 | 25 | 3.06/1 | 25 | 2 ⎫ |
|   |      |    |    |        | 45 | 2  ⎬ successively |
|   |      |    |    |        | 75 | 2  ⎪ |
|   |      |    |    |        | 100 | 2 ⎭ |
| C | 27.6 | 50 | 28 | 3.07/1 | 35 | 1 ⎫ |
|   |      |    |    |        | 75 | 1 ⎬ successively |
|   |      |    |    |        | 100 | 1 ⎪ |
|   |      |    |    |        | Ambient | 12 ⎭ |

TABLE IV-continued

| Run | $C_6F_5OH$ (g) | $SF_4$ (g) | HF (g) | $SF_4/C_6F_5OH$ Mole Ratio | Temp. (° C) | Time (Hrs) |
|---|---|---|---|---|---|---|
| | | | | | air | |

*Reaction mixture held at room temperature for 48 hours without agitation.

In run A the vented reactor was emptied and rinsed with 50 ml of dichloromethane and the rinse solution was added to the previously collected product. The composite product was stored overnight in contact with 25 g of sodium fluoride pellets. Fractional distillation of the product yielded 14.25 g of a liquid fraction, bp 73°/10 mm and $n_D^{25}$ 1.3992. VPC indicated the product to be substantially pure, and DTA indicated a melting point at −12° to −9° and a glass transition temperature (Tg) at −83°. This product was identified by EA, IR, MS and fluorine NMR analyses as 1-pentafluorophenoxy-1,2,3,4,4,5,6-heptafluoro-2,5-cyclohexadiene.

Calcd for $C_{12}F_{12}O$: C, 37.11; H, 0.00; F, 58.76, MW, 388; Found: C, 37.39; H, 0.23; F, 58.57; MW, 388.

In run B the vented product was initially steam-distilled to give 13.66 g of nonaqueous distillate and 6.1 g of syrupy residue. The distillate was fractionally distilled at atmospheric pressure to yield 5.75 g of material, bp 184°–187°, indicated by VPC to consist of about 67% of 1-pentafluorophenoxy-1,2,3,4,4,5,6-heptafluoro-2,5-cyclohexadiene. The remainder was identified, via a sample isolated by VPC and IR, MS and fluorine NMR analyses as probably a mixture of $C_{12}F_{12}O$ isomers, believed to be 1-pentafluorophenoxy-2,3,4,5,5,6,6-heptafluoro-1,3-cyclohexadiene and 1-pentafluorophenoxy-2,3,3,4,4,5,6-heptafluoro-1,5-cyclohexadiene. The steam distillate residue was indicated to be polymeric material containing 30 carbons in five interconnected perfluoro six-membered rings.

In run C the vented product was steam-distilled to yield 21.6 g of nonaqueous distillate and 5.36 g of residue. Fractional redistillation of the steam distillate yielded 7.05 g of unreacted pentafluorophenol and 10.86 g of about 98% pure 1-pentafluorophenoxy-1,2,3,4,4,5,6-heptafluoro-2,5-cyclohexadiene.

1-Pentafluorophenoxy-1,2,3,4,4,5,6-heptafluoro-2,5-cyclohexadiene was polymerized to the extent of about 18% when heated from 132° to 150° over a period of about 3.5 hours with di(t-butyl) peroxide initiator. Nearly three-fourths of the polymer was in the form of a clear viscous syrup which was an effective plasticizer at the 9–10% level for polystyrene, poly(methyl methacrylate) and poly(vinyl acetate). The remainder of the polymer was an acetone-soluble solid which was an effective water repellant for cellulose filter paper.

1-Pentafluorophenoxy-1,2,3,4,4,5,6-heptafluoro-2,5-cyclohexadiene itself, and the polymeric nonsteam distillable residue obtained in run B were also effective plasticizers for each of polystyrene, poly(methyl methacrylate) and poly(vinyl acetate) at the 9–10% level.

EXAMPLE 9

Reaction of 4-Chlorotetrafluorophenol with $SF_4$ in HF

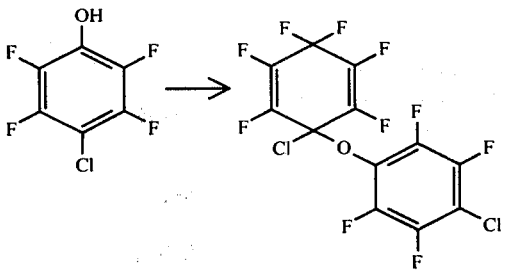

Following the general procedure of Example 1, 4-chlorotetrafluorophenol ($C_6ClF_4OH$) was reacted with $SF_4$ in HF. The data for three runs is given in Table V.

TABLE V

| Run | $C_6ClF_4OH^*$ (g) | $SF_4$ (g) | HF (g) | $SF_4/C_6ClF_4OH$ Mole Ratio | Temp. (° C) | Time (Hrs.) |
|---|---|---|---|---|---|---|
| A | 30 | 50 | 30 | 3.07/1 | Ambient air | 16 |
| B | 30 | 55 | 30 | 3.40/1 | 35 | 1) successively |
| | | | | | 65 | 2) ively |
| C | 40 | 25 | 40 | 1.15/1 | 50 | 3 |

*87% pure, with other isomers present.

In run A the vented product gave 25.4 g of nonaqueous steam distillate and 3.7 g of nonflowable syrupy residue. The steam distillate was fractionally redistilled to yield 12.55 g of liquid product, bp 67.0°–68.8°/0.-48–0.55 mm and $n_D^{25}$ 1.4468, which by DTA showed no melting point, Tg at −68° and bp/760 mm at 243–255°. This product was indicated by VPC, MS and fluorine IR analysis to be primarily of the probable structure of 1-(4-chlorotetrafluorophenoxy)-1-chloro-2,3,4,4,5,6-hexafluoro-2,5-cyclohexadiene although alternate isomeric structures cannot be ruled out.

Similarly, in run B, the fractionated liquid product, bp 58°–66°/0.24–0.35 mm, was indicated by VPC to contain two $C_{12}Cl_2F_{10}O$ isomers in about 93/7 ratio.

In run C the steam distillation gave 25.8 g of nonaqueous distillate and 7.2 g of soft, adhesive, syrupy residue. Fractionation of the distillate gave 18.44 g of $C_{12}Cl_2F_{10}O$ product, bp, 68°–70°/0.50–0.55 mm.

Polystyrene, poly(methyl methacrylate) and poly(vinyl acetate) were each found to be effectively plasticized by addition of 9–10% of 1-(4-chlorotetrafluorophenoxy)-1-chloro-2,3,4,4,5,6-hexafluoro-2,5-cyclohexadiene. The hexadiene was polymerized to the extent of 24% when heated at 148°–150° over a period of about 6.5 hours with di(t-butyl) peroxide initiator, the polymer being a soft, clear, light brown material.

EXAMPLE 10

Reaction of Dichlorotrifluorophenol with $SF_4$ in HF

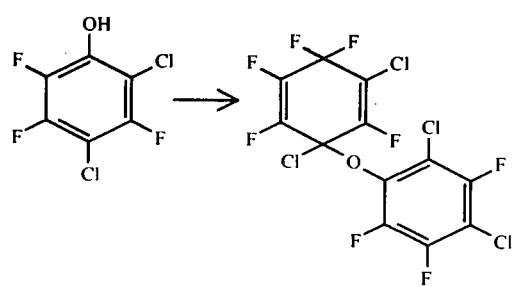

A mixture of isomeric dichlorotrifluorophenols ($C_6Cl_2F_3OH$) containing 75% of 2,4-dichlorotrifluorophenol was reacted with $SF_4$ in HF. The data for two runs is given in Table VI.

TABLE VI

| Run | $C_6Cl_2F_3OH$ (g) | $SF_4$ (g) | HF (g) | $SF_4/C_6Cl_2F_3OH$ Mole Ratio | Temp. (° C) | Time (Hrs.) |
| --- | --- | --- | --- | --- | --- | --- |
| A | 29.5 | 60 | 30 | 4.1/1 | Ambient air | 16 |
| B | 29.5 | 60 | 30 | 4.1/1 | 25 | 2) successively |
|  |  |  |  |  | 45 | 2) |
|  |  |  |  |  | 75 | 2) |
|  |  |  |  |  | 100 | 2) |

In run A the vented crude product yielded 11.2 g of nonaqueous steam distillate and 4.8 g of brown semisolid residue. Fractionation of the distillate gave a small amount of dichlorotrifluorophenol and 7.81 g of dimeric product, bp 95°–98°/0.25–0.33 mm and $n_D^{25}$ 1.4897.

EA. Calcd for $C_{12}Cl_4F_8O$: C, 31.72; Cl, 31.28; F, 33.48; Found: C, 31.88; Cl, 31.52; F, 32.51.
VPC indicated the presence of three principal components in about 64/21/12 ratio, and DTA showed Tg's at −50° and +30°.

In run B 15.1 g of nonaqueous steam distillate and 5.9 g of residue were obtained. Fractionation of the distillate yielded 8.74 g of principal product, bp, 99°–104°/0.25–0.57 mm. The main component of this product, isolated by preparative VPC, was indicated by MS, IR and DTA to be 1-(2,4-dichlorotrifluorophenoxy)-1,3-dichloro-2,4,4,5,6-pentafluoro-2,5-cyclohexadiene, Tg −50°, although alternate isomeric structures cannot be ruled out.

EA. Calcd for $C_{12}Cl_4F_8O$: C, 31.72; Cl, 31.28; F, 33.48; Found: C, 31.94; Cl, 31.14; F, 33.48.

Polystyrene, poly(methyl methacrylate) and poly(vinyl acetate) were each found to be effectively platicized by 9–10% of 1-(2,4-dichlorotrifluorophenoxy-1,3-dichloro-2,4,4,5,6-pentafluoro-2,5-cyclohexadiene. The hexadiene was polymerized to the extent of 37% when heated in the range of 129°–155° over a period of about 4 hours with di(t-butyl) peroxide initiator. The polymer was a tacky, soft brown material which was soluble in acetone. Filter paper treated with this polymer became water repellant.

EXAMPLE 11

Reaction of Trichlorodifluorophenol with $SF_4$ in HF

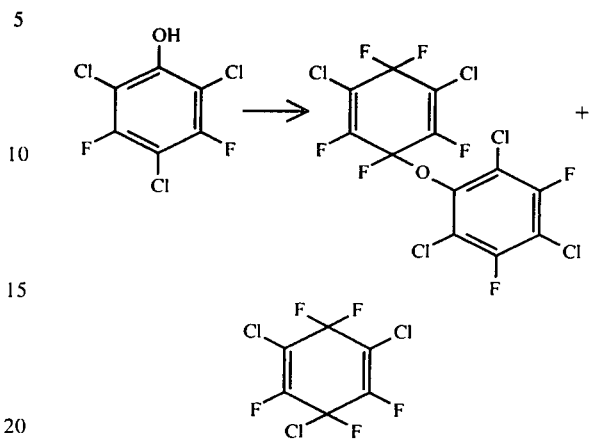

A mixture of isomeric trichlorodifluorophenols ($C_6Cl_3F_2OH$) containing 93% of 2,4,6-trichlorodifluorophenol was reacted with $SF_4$ in HF. The data for three runs is given in Table VII.

TABLE VII

| Run | $C_6Cl_3F_2OH$ (g) | $SF_4$ (g) | HF (g) | $SF_4/C_6Cl_3F_2OH$ Mole Ratio | Temp. (° C) | Time (Hrs.) |
| --- | --- | --- | --- | --- | --- | --- |
| A | 32 | 60 | 35 | 4.0/1 | Ambient air | 16 |
| B | 32 | 60 | 35 | 4.0/1 | 25 | 1) |
|  |  |  |  |  | 45 | 1) successively |
|  |  |  |  |  | 75 | 1) ively |
|  |  |  |  |  | 100 | 2) |
| C | 50 | 15 | 40 | 0.67/1 | 50 | 1) Successively |
|  |  |  |  |  | 100 | 2) ively |

In run A the vented crude product yielded 21.2 g of nonaqueous distillate and 7.8 g of brown semisolid residue. Fractionation of the distillate gave 6.17 g of unreacted trichlorodifluorophenol, bp 70°–7°/16 mm, and 8.64 g of a new product, bp 51°–2°/16 mm.

In run B 18.3 g of nonaqueous steam distillate and 11.7 g of residue were obtained. The distillate yielded a main product fraction, bp. 52°–52.8°/16 mm, which by VPC contained two components, presumably isomers, in about a 90/10 ratio.

EA. Calcd for $C_6Cl_3F_5$: C, 26.33; Cl, 38.94; F, 34.73; Found: C, 26.10; Cl, 39.26; F, 34.70.

The major component, which was identical to that of run A, was indicated by fluorine NMR to be 1,3,5-trichloro-1,2,4,4,6-pentafluoro-2,5-cyclohexadiene. The steam distillation residue was fractionally distilled to yield 3.05 g of liquid-solid mixture, bp 120°–134°/0.08 mm. EA and fluorine NMR indicated this fraction to be mainly of the structure of 1-(2,4,6-trichlorodifluorophenoxy)-3,5-dichloro-1,2,4,4,6-pentafluoro-2,5-cyclohexadiene, although alternate isomeric structures cannot be ruled out.

In run C the $C_6Cl_3F_5$ component was recovered in 20.6% conversion, which indicates that a large excess of $SF_4$ is not necessary for this reaction to proceed.

EXAMPLE 12

Reaction of Dichlorodifluorophenol with SF$_4$ in HF

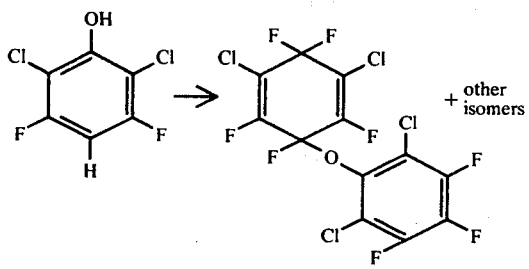

A mixture of isomeric dichlorodifluorophenols (C$_6$HCl$_2$F$_2$OH) containing 65% of 2,6-dichloro-3,5-difluorophenol was reacted with SF$_4$ in HF, the reaction mixture containing 30 g of C$_6$HCl$_2$F$_2$OH, 65 g of SF$_4$ (SF$_4$/C$_6$HCl$_2$F$_2$OH mole ratio = 4.0/1) and 30 g of HF, at 45° for 1 hour, 75° for 1 hour and 100° for 2 hours. The vented crude product yielded 9.6 g of nonaqueous steam distillate and 17.4 g of dark brown resinous residue. The distillate yielded a principal liquid fraction, bp, 87.7°–89°/0.12–0.17 mm, which was indicated by IR to contain a cyclohexadiene structure.

EA. Calcd for C$_{12}$Cl$_4$F$_8$O: C, 31.72; Cl, 31.28; F, 33.48; Found: C, 32.14; Cl, 30.75; F, 33.55.

The steam distillation residue yielded only a small amount of distillable material, bp 135°/0.10 mm, which contained 27.18% fluorine.

EXAMPLE 13

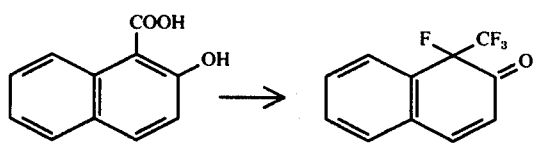

An air-free mixture of 28.2 g of 2-hydroxy-1-naphthoic acid, 108 g of SF$_4$ (SF$_4$/hydroxynaphthoic acid mole ratio = 7.6/1) and 40 g of HF was agitated at ambient air temperature for 16 hours. The vented reaction mixture was suspended in water, neutralized with sodium bicarbonate and extracted with dichloromethane. The residue from the extract after removal of dichloromethane was 15.4 g of brown solid which yielded only a trace of distillate when heated to 228° under reduced pressure of less than 1 mm. IR analysis of the distillate was indicative of the probable presence of 1-fluoro-1-trifluoromethyl-2-keto-1,2-dihydronaphthalene.

EXAMPLE 14

Reaction of 2,4,5-Trichlorophenol with SF$_4$ in HF

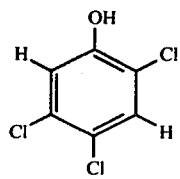

An air-free mixture of 39.5 g of 2,4,5-trichlorophenol, 45 g of SF$_4$ (SF$_4$/trichlorophenol mole ratio equals 2.10/1), 30 g of HF and 60 ml of dichloromethane was agitated in a sealed Hastelloy reactor at −10° for 4 hours, 0° for 4 hours and ambient air temperature for 8 hours. The vented product was steam distilled and, aside from recovered dichloromethane, only 0.31 g of distillate was obtained. The yellow solid (39.5 g) remaining was separated into an acetone soluble fraction (A; orange-brown solid; 75%) and an acetone insoluble fraction (B; yellow solid; 25%). B, after a recrystallization from hot n-butanol, analyzed approximately for (C$_{12}$H$_2$Cl$_6$SO)$_n$ where n = ~ 2.5.

Anal. Calcd. for C$_{12}$H$_2$Cl$_6$SO: C, 35.38; H, 0.49; Cl, 52.33; S, 7.86; MW, 403.5/unit; Found: C, 35.15; H, 0.58; Cl, 50.94; S, 7.88; F, 0.51; MW, 987 (boiling 1-butanol).

IR analysis indicated the presence of unsaturated =CH (3.23 μ) and aromatic C=C (6.32, 6.47 μ). ESCA analysis indicated that sulfur was divalent. Fraction A was further separated into an alkaline soluble and an alkaline insoluble fraction based on its solubility in 10% potassium hydroxide solution. Neither of these fractions was completely characterized. The alkaline insoluble cut analyzed approximately for C$_{18}$H$_8$Cl$_7$F$_3$O$_2$S or C$_{18}$H$_6$Cl$_7$F$_3$O$_2$S based on its elemental and molecular weight determinations; ESCA analysis indicated the sulfur was divalent. The alkaline soluble fraction, which was essentially free of sulfur, was similarly analyzed, and shown by EA, molecular weight and neutral equivalent analyses to contain at least two constituents having 12 and 18 carbon atoms.

EXAMPLE 15

Reaction of 2,3,5,6-Tetramethylphenol with SF$_4$ in HF

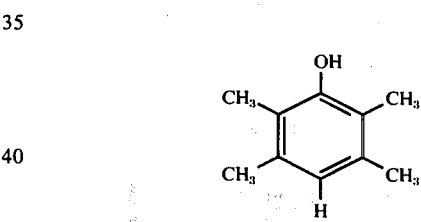

2,3,5,6-Tetramethylphenol [(CH$_3$)$_4$C$_6$HOH] was reacted with SF$_4$ in HF, the data for two runs being given in Table VIII.

TABLE VIII

| Run | (CH$_3$)$_4$-C$_6$HOH (g) | SF$_4$ (g) | HF (g) | SF$_4$/(CH$_3$)$_4$C$_6$HOH Mole Ratio | Temp. (° C) | Time (Hrs.) |
|---|---|---|---|---|---|---|
| A | 30 | 65 | 40 | 3/1 | 10 | 2 |
|   |    |    |    |     | 20 | 2 |
|   |    |    |    |     | Room | 12 |
| B | 30 | 65 | 40 | 3/1 | Room | 16 |

In these runs, steam distillation was omitted.

In run A the vented crude product was mixed into 150 ml of dichloromethane and 50 g of NaF pellets was added to scavenge HF. The mixture was then filtered and the dichloromethane solution concentrated on a steam bath. The residue was 25 g of yellow-brown solid which was polymeric in nature, forming brittle films on evaporation of a solution in tetrahydrofuran, having an average molecular weight of about 1300 and containing C, H, F, O and S. The product was found by IR and NMR to have no hydroxyl groups, predominant C-CH$_3$ groupings and strong

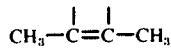

structural entities.

In run B the vented crude product (24.2 g) was washed with water, filtered, and separated into three fractions on the basis of its solubility in selected solvents. Eleven percent (m, >190°) was insoluble in carbon disulfide but soluble in methylene chloride (A); 17.5% (slow darkening >225°, but did not melt) was soluble in carbon disulfide but insoluble in acetone (B); 60% (slow darkening at about 228°, but did not melt) was soluble both in carbon disulfide and in acetone (C).

The proton NMR spectra of all three fractions were rather similar; each contained two broad peaks in ratios of ~13:1 to 15:1. IR analysis of all three fractions was similar, with saturated CH (3.44 μ), unsaturated C=CF (weak 5.93 μ), C=C (broad at 6.20, 6.46 μ), and CCH$_3$ (strong, 7.25 μ). Each, except possibly (A), analyzed approximately for C$_{30}$H$_{39}$F$_3$OS$_2$.

Anal. Calcd. for C$_{30}$H$_{39}$F$_3$OS$_2$: C, 67.16; H, 7.28; F, 10.63; S, 11.94. Found (A): C, 63.64; H, 5.37; F, 12.85; S, 7.69; MW, 2737; Found (B): C, 67.62; H, 5.37; F, 11.62; S, 11.80; MW, 5785; Found (C); C, 65.00; H, 5.72; F, 12.61; S, 12.98; MW, 928;

A possible structure for this polymer is:

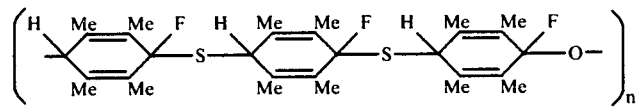

where n for (A) = 5.1 n for (B) is 10.8 and n for (C) is 1.7.

EXAMPLE 16

Reaction of p-Methoxyphenol with SF$_4$ in HF

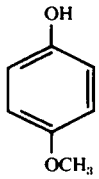

An air-free mixture of 12.4 g of p-methoxyphenol, 11 g of SF$_4$ (SF$_4$/methoxyphenol mole ratio = 1/1), and 60 g of HF was agitated at ambient air temperature for 16 hours. The vented, yellow colored product was extracted for 16 hours with boiling acetone in a continuous extractor. The insoluble fraction (3.9 g) was a yellow-orange solid, η$_{inh}$ (0.1% dimethylsufoxide), 0.33. The acetone soluble fraction was recovered as a clear, orange-brown, brittle film, η$_{inh}$ (0.1% dimethylsulfoxide), 0.14. The average molecular weight (boiling acetonitrile) of this fraction was about 1775. IR of both fractions was very similar and indicated the presence of methoxyl, hydrogen bonded hydroxyl and a conjugated diene system.

EA Calcd. for (C$_{14}$H$_{12}$F$_3$S$_{1.5}$O$_4$)$_n$: C, 48.14; H, 3.44; F, 16.33; S, 13.75; Found (acetone insol): C, 50.82; H, 3.10; F, 16.18; S, 13.11; Found (acetone sol): C, 49.84; H, 3.24; F, 16.77; S, 13.74.

EXAMPLE 17

Reaction of Methyl Salicylate with SF$_4$ in HF

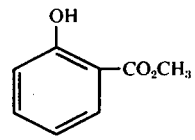

An air-free mixture of 30.4 g of methyl salicylate, 54 g of SF$_4$ (SF$_4$/salicylate mole ratio = 2.5/1) and 45 g of HF was agitated at 40° for 1 hour, 65° for 1 hour, 80° for 2 hours and at ambient air temperature for an additional 12 hours. The vented reaction mixture was extracted with dichloromethane and the extract concentrated to yield 32.8 g of an orange-brown colored polymeric solid. This material was fractionally separated by solvent extraction: 15% was soluble in acetone but insoluble in diethyl ether and in boiling methanol (A); 35–40% was soluble in acetone, insoluble in diethyl ether but soluble in boiling methanol (B); 25–30% was soluble both in acetone and diethyl ether (C).

A. analyzed approximately for (C$_8$H$_6$F$_2$O$_2$S)$_n$, where n = ~ 25.

Anal. Calcd. for (C$_8$H$_6$F$_2$O$_2$S)$_n$: C, 47.06; H, 2.94; F, 18.63; S, 15.69; Found: C, 45.93; H, 1.95; F, 21.83; S, 13.47; MW, 5100 (boiling acetone).

IR analysis of (A) indicated the presence of both unsaturated =CH (3.25μ) and saturated CH (3.38μ); carbonyl (5.77, 5.92μ); C=C (aromatic) (6.23, 6.67μ) and C-F and/or C-O-C (broad 8.75μ). Proton NMR, analyses (in (CD$_3$)$_2$S=O) indicated the probable presence of OCH$_3$; a second very broad peak was adjacent to the first one. On heating, the polymer initially darkened at ~ 208°, with gradual softening to 245°, followed by gradual hardening from 245°–270°, where forming occurred.

A possible structure for this polymer fraction is

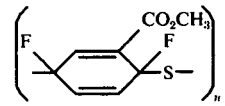

B. analyzed only approximately for the same polymer shown and was obviously a mixture of products.

Anal. Calcd. for (C$_8$H$_6$F$_2$O$_2$S)$_n$: C, 47.06; H, 2.94; F, 18.63; S, 15.69; Found: C, 47.38; H, 2.60; F, 23.08; S, 9.54; MW, 1020.

C. had the following elemental analysis:

Found: C, 39.81; H, 1.41; F, 34.58; S, 16.47; MW, 666.

This material softened, 65° and foamed from 76°–108°. IR analysis was complicated but was generally similar to that of (A). Fluorine NMR (in CH$_2$Cl$_2$)

revealed the presence of one broad peak plus several very small peaks.

A possible structure for the polymer fraction is

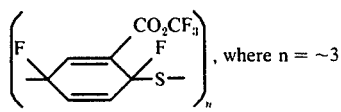, where n = ~3 where $n = \sim 3$

Calcd. for $(C_8H_3F_5O_2S)_n$: C, 37.2; H, 1.2; F, 37.0; S, 12.4.

Another possible structure for the polymer fraction

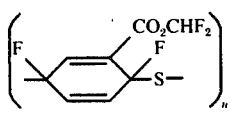

Calcd. for $(C_8H_4F_4O_2S)_n$: C, 40.0; H, 1.7; F, 31.7; S, 13.3.

Another possible structure for this material follows:

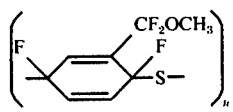

Calcd. for $(C_8H_6F_4OS)_n$: C, 42.5; H, 2.7; F, 33.6; S, 14.2.

In a separate experiment no signficant reaction was obtained between methyl salicylate and $SF_4$ in HF at 25° for 16 hours.

EXAMPLE 18

Reaction of o-Phenylphenol with $SF_4$ in HF

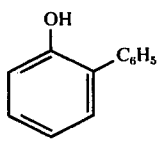

An air-free mixture of 17 g of o-phenylphenol, 11g of $SF_4$ ($SF_4$/phenylphenol mole ratio = 1/1) and 60g of HF was agitated an ambient air temperature over a 16 hours period, and then held in the reactor without agitation for 48 hours at room temperature before removal of the volatile material by venting. The residue was warmed moderately to remove much of the remaining hydrogen fluoride. The viscous residue was treated with sodium fluoride to remove the hydrogen fluoride remaining. The product was now added portionwise to 600 ml of acetone with stirring; filtration yielded 18.1 g of tan colored solids. Nothing was extracted on suspending this product in 200 ml of carbon disulfide, indicating the absence of elemental sulfur. A test portion was dissolved in trifluoroacetic acid; evaporation of the solvent yielded a clear, hard brittle film which melted at 230°–237°, but the resulting melt was too viscous to flow. The product was soluble in 10% KOH solution on gentle warming.

EA Calcd. for $(C_{24}H_{16}F_2O_2S)_n$: C, 70.93; H, 3.92; F, 9.36; S, 7.88; Found: C, 69.74; H, 4.15; F, 6.98; S, 8.64.

An ebullioscopic molecular weight $(\overline{M}_n)$ value in $CF_3CO_2H$ was dependent on the boiling time and/or solution concentration.

| CONC % by Wt. | $\overline{M}_n$ |
|---|---|
| 0.37 | 1980 |
| 0.57 | 1655 |
| 0.77 | 1320 |
| 0.94 | 1185 |
| 1.18 | 1195 |
| Zero Conc. (by graph) | 3800 |

IR indicated the presence of unsaturated HC at $3.25\mu$ and aromatic C = C at 6.32, 6.65 and 6.72; hydroxyl was present.

Although the invention has been described and exemplified by way of specific embodiments, is is not intended that it be limited thereto. As will be apparent to those skilled in the art, numerous modifications and variations of these embodiments can be made without departing from the spirit of the invention or the scope of the following claims.

We claim:
1. A method for the oxidative fluorination of phenols which comprises reacting a 3,5-difluorophenol of the formula

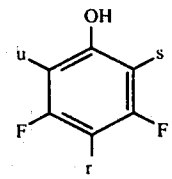

where
  s and u, alike or different, are chlorine, bromine or fluorine, and
  r is hydrogen, chlorine, or fluorine
with 0.1 to 10 moles per mole of starting phenol of sulfur tetrafluoride in sufficient hydrogen fluoride to keep the reactants in solution at a temperature of 0° to 100° C, thereby forming 1,1,3,5-tetrafluoro-2,4,6-trihalo-4-(3,5-difluoro-2,4,6-trihalophenoxy)-2,5-cyclohexadiene of the structure

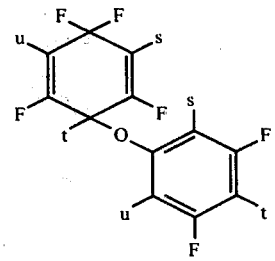

where
  s and u are as specified above, and
  t is chlorine, or fluorine, provided that
    when r is hydrogen or fluorine, t is fluorine, and,
    when r is chlorine, t is chlorine.
2. The method of claim 1 in which the temperature is ambient to 100° C.

* * * * *